United States Patent [19]

Sikes

[11] Patent Number: 5,051,401
[45] Date of Patent: Sep. 24, 1991

[54] INHIBITION OF MINERAL DEPOSITION BY PHOSPHORYLATED AND RELATED POLYANIONIC PEPTIDES

[75] Inventor: C. Steven Sikes, Mobile, Ala.

[73] Assignee: University of South Alabama, Mobile, Ala.

[21] Appl. No.: 334,456

[22] Filed: Apr. 7, 1989

[51] Int. Cl.$^5$ .............................................. C02F 5/10
[52] U.S. Cl. ........................................ 514/7; 424/49; 424/54; 514/12-17; 514/824; 514/901; 530/324-330; 528/321; 427/384; 433/215
[58] Field of Search .................. 514/7, 12-17, 514/824, 901; 424/49, 54; 530/324-330; 433/215; 427/384

[56] References Cited

U.S. PATENT DOCUMENTS

| | | | |
|---|---|---|---|
| 4,339,431 | 1/1982 | Gaffar | 424/49 |
| 4,363,797 | 12/1982 | Jacquet et al. | 424/72 |
| 4,534,881 | 8/1985 | Sikes et al. | 252/175 |
| 4,585,560 | 4/1986 | Sikes et al. | 252/180 |
| 4,587,021 | 5/1986 | Wheeler et al. | 252/180 |
| 4,603,006 | 7/1986 | Sikes et al. | 252/180 |
| 4,643,988 | 2/1987 | Segrest et al. | 514/12 |
| 4,866,161 | 9/1989 | Sikes et al. | 530/329 |
| 4,868,287 | 9/1989 | Sikes et al. | 530/329 |

OTHER PUBLICATIONS

Hay, D. I. et al., Inorg. Persp. Biol. Med. 2, 271-285 (1979).
Hay, D. I. et al., Calcif. Tiss. Int. 40, 125-132 (1987).
"Surface Reactive Peptides and Polymers", A Symposium Sponsored by the Division of Industrial and Engineering Chemistry of the American Chemical Society (Apr. 12, 1989).

Primary Examiner—Earl Nielsen
Assistant Examiner—Frederick Krass
Attorney, Agent, or Firm—Oblon, Spivak, McClelland, Maier & Neustadt

[57] ABSTRACT

A poly-amino acid compound capable of inhibiting mineral deposition, which has the structure:

$$\text{poly } (X)_m(Y)_n$$

where
  each X independently is aspartate, glutamate, glutamine, asparagine, or anionic derivatives of these amino acids, or phosphoserine,
  each Y independently is a phosphorylated amino acid such as phosphoserine, phosphohomoserine, phosphotyrosine, phosphothreonine, phosphoglutamine, phosphoasparagine, or mixtures of these residues,
  $m$ is 2 to 150,
  $n$ is 1 to 3, and
  $n+m$ is $\geq 5$, and
salts of these peptides.

19 Claims, 4 Drawing Sheets

INHIBITION OF MINERAL DEPOSITION BY PHOSPHORYLATED AND RELATED POLYANIONIC PEPTIDES

Work for the present invention was supported in part by grants from the Alabama Research Institute, The National Science Foundation, the Office of Naval Research and the Mississippi-Alabama Sea Grant Consortium.

BACKGROUND OF THE INVENTION

1. Field of the Invention

This invention relates to the discovery of new phosphorylated, polyanionic peptides that are surprisingly powerful inhibitors of mineral formation, particularly the crystallization of calcium carbonate and calcium phosphate. The molecules may be useful in a variety of applications including but not limited to tartar control, prevention of industrial scaling, use as dispersants, corrosion inhibition, prevention of pathologic calcification, and control of biofouling.

2. Discussion of Background

Biological mineralization is a fundamental process in nature. Formation of bones and teeth from calcium phosphate and formation of shells and reefs from calcium carbonate are but two examples of this process.

Unfortunately, mineral deposits also frequently occur where they are not wanted. In the body, mineral deposition may contribute to dental plaque, hardening of the arteries, various organ stones, and failure of prosthetic devices like implanted heart valves. In the marine environment, the biomineral structures may cause problems as in the case of barnacles growing on the hulls of ships, adding extra bulk and creating drag. In industry, mineral scale forms on surfaces of cooling towers and other devices preventing their proper operation as heat exchangers and frequently promoting localized corrosion.

Because of the problems associated with unwanted mineral deposition, much effort has been devoted to finding mineralization inhibitors, particularly in industry, that might be used to prevent harmful mineral formation.

Molecules for prevention of mineral deposition have ranged from simple ions like $Mg^{+2}$ (Pytkowicz, R.M., J. Geol. 73, 196-199 (1965)) and $PO_4^{3-}$ or pyrophosphate (Simkiss, K., Biol. Rev. 39, 487-505 (1964)) to more complex organic materials. Inhibition by simple ions is based on the ability of these ions to interfere with the orderly formation of the crystalline lattice of the mineral, such as $CaCO_3$. In addition, phosphate and polyphosphates have the property of protecting metallic surfaces by forming very thin films that cover potential sites of corrosion on the surfaces.

Phosphonates were introduced in the late 1960's (Ralston, U.S. Pat. No. 3,336,221 (1967)). These are small organic molecules with $PO_3$ groups attached directly to a central carbon atom via a covalent bond to phosphorus. The phosphonates are very effective inhibitors of crystallization that work by adsorbing to crystal surfaces. Hydroxyethylidene diphosphonate (HEDP) is perhaps the most widely used phosphonate, still among the most powerful inhibitors of $CaCO_3$ formation known.

Use of phosphonates has some disadvantages though. For example, phosphonates can be degraded during chlorination which in turn may lead to elevated phosphates and associated phosphate scales. Phosphonates themselves may also precipitate under common operating conditions. HEDP is an exceptionally effective inhibitor of crystal nucleation on a weight basis as shown by its effect on lengthening the induction period prior to crystal growth, but it is not at all effective at inhibiting crystal growth after it begins, (Sikes and Wheeler, CHEMTECH 1988, pp. 620-626 (1988).)

More recently, as a result of continuing efforts to identify better inhibitors, polyacrylat and other polyanionic materials have been identified (Rohm and Haas Company, Technical Bulletin CS-513A (1985), *Fong and Kowalski*, U.S. Pat. No. 4,546,156 (1985)). In the 1980's, antiscaling and anticorrosion technology has been based increasingly on use of synthetic polymers under alkaline conditions. The current trend in synthetic polymers for water treatment is the use of random copolymers or terpolymers with alternating side groups of $COO^-$ with groups like $OH$, $CH_3$, $PO_3^{2-}$, $SO_3^{2-}$ etc.

Among the newest approaches to developing mineral deposition inhibitors involves naturally-occurring proteins and polysaccharides that regulate mineral formation by organisms (U.S. Pat. Nos. 4,534,881 (1985), 4,585,560 (1986); 4,603,006 (1986); and 4,587,021 (1986) by C.S. Sikes and A.P. Wheeler). This approach led to the identification of a new class of polyanionic/hydrophobic peptides that are even more powerful inhibitors of crystallization on a weight basis than the natural protein (U.S. application Ser. No. 07/088,247).

In spite of the above approaches to solving the problems of unwanted mineral deposition, there remains a strong need for new and more powerful inhibitors of mineral deposition which could be used in the body, in a marine environment, or industrially, etc.

Now the inventor has discovered that certain phosphorylated, polyanionic peptides are unexpectedly much more effective inhibitors, on a weight basis, than other similar peptides. They are particularly effective inhibitors of calcium phosphate formation, but also of calcium carbonate formation and other mineral depositions as well.

A clue to the identity of the new inhibitors was taken from the report that certain protein inhibitors of calcium deposition from saliva had two phosphoserine residues adjacent to an N-terminal aspartic acid residue (Hay, D.I., et al., Inorg.Persp.Biol.Med.2, 271-285 (1979)). This idea was then contemplated along with the concept that polyelectrolytic polypeptides may adsorb to surfaces by binding only by a few monomers at one end of the molecule, with the rest of the molecule suspended unbound from the surface (Juriaanse et al., J. of Coll. and Interface Sci. 76, 212-219 (1980)). The inventor explored the idea that the terminal residues may be critical in binding of peptides to crystals. That phosphoserine itself is involved in some way in inhibitory activity of proteins and peptides is suggested by Schlesinger et al., in *Chemical Aspects of Regulation of Mineralization*, C.S. Sikes and A. P. Wheeler, eds., 33-38, 1988 and A. P. Wheeler and C. S. Sikes, in *Chemical Perspectives on Biological Mineralization*, S. Mann et al., eds., in press 1989.

In short, the present invention identifies new polyanionic polypeptide molecules. These materials preferably contain one to three phosphoserine residues on one end of the molecule. The rest of the molecule is preferably composed of aspartic acid residues. Sulfated, phosphonated, and sulfonated derivatives of serine and other amino acids are also contemplated for inclusion at one of the terminal regions of the molecules.

The N-terminally phosphorylated polyanionic polypeptides of this invention have not been specifically described before. Such a molecule appears to fall broadly within the claims of U.S. Pat. No. 4,534,881 (Sikes and Wheeler 1985). However, the present molecules were not specifically identified therein and there was no suggestion of any special activity inherent in them.

Molecules of H—(Ala)$_m$—(Asp)$_n$—(pSer)$_x$—OH where m = 2–10, n = 10–60, and x = 2–5 were claimed in U.S. application Ser. No. 07/088,247 (Sikes and Wheeler, 1988). However, these molecules contain hydrophobic clusters, unlike the molecules herein. In addition, there was no mention therein of a molecule containing only one N-terminal phosphoserine residue, as in this invention.

SUMMARY OF THE INVENTION

Figure 1:
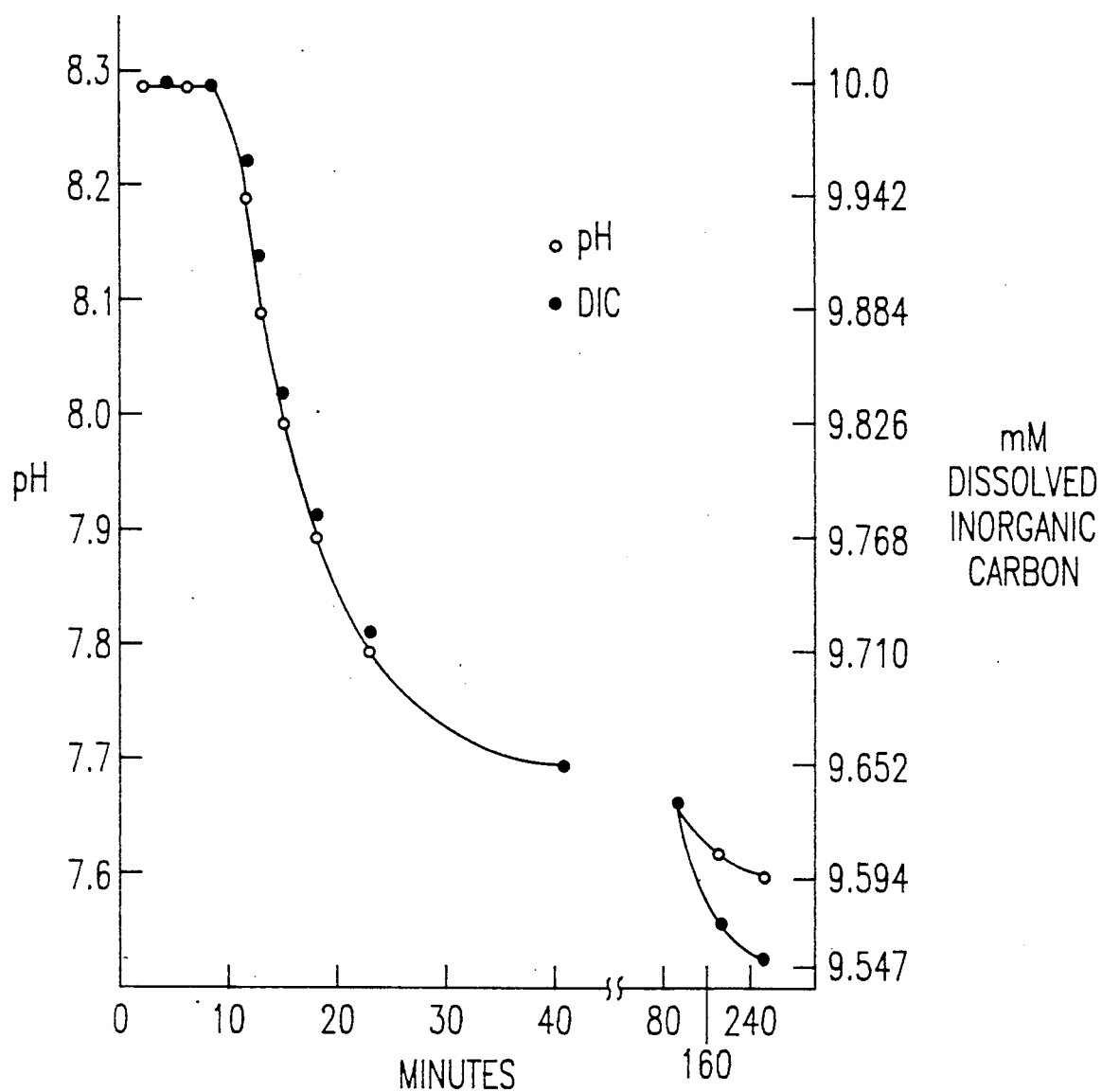
FIG. 1: Data obtained from a pH-drift crystallization assay.

Accordingly, it is an object of the present invention to provide new and improved materials for inhibiting mineral deposition.

It is another object of the present invention to provide materials for prevention of formation of calculus or plaque on teeth.

It is another object of the present invention to provide materials which can prevent mineralization in a marine environment, such as by prevention of barnacle accumulation.

It is yet another object of the present invention to provide materials which can effectively prevent mineralization on prosthetic devices implanted in the body.

It is yet another object of the present invention to provide materials for prevention of mineralization in arteries, associated with arteriosclerosis, or atherosclerosis.

It is yet another object of the present invention to provide for materials which can prevent mineralization in an industrial setting, such as scaling in water treatment plants.

It is yet another object of the present invention to provide for materials which can prevent corrosion of metallic surfaces.

It is yet another object of the present invention to provide for methods of prevention of the abovementioned types of mineralization.

These and other objects of the present invention which will hereinafter become more readily apparent, have been accomplished by providing new polypeptide materials which have the following general formula:

poly $(X)_m(Y)_n$ where
each X independently is aspartate, glutamate, glutamine, asparagine, or anionic derivatives of these amino acids, or phosphoserine
each Y independently is a phosphorylated amino acid such as phosphoserine, phosphohomoserine, phosphotyrosine, phosphothreonine, phosphoglutamine, phosphoasparagine or mixtures of these residues,
m is 2 to 150,
n is 1 to 3, and
n+m is >5, and
salts of these peptides.

The present invention is also directed to compositions containing these materials, such as dentifrices and mouthwashes for oral application.

A more complete appreciation of the invention and many of the attendant advantages thereof will be readily perceived as the same becomes better understood by reference to the following detailed description of preferred embodiments thereof.

DETAILED DESCRIPTION OF THE PREFERRED EMBODIMENTS

The general structure of the polypeptides of the present invention is as follows:

poly $(X)_m(Y)_n$ where
each X independently is aspartate, glutamate, glutamine, asparagine, or anionic derivatives of these amino acids, or phosphoserine
each Y independently is a phosphorylated amino acid such as phosphoserine, phosphohomoserine, phosphotyrosine, phosphothreonine, phosphoglutamine, phosphoasparagine, or mixtures of these residues,
m is 2 to 150,
n is 1 to 3, and
n+m is >5, and
salts of these peptides, particularly those with physiologically acceptable anions and cations.

In the above formula, both X and Y may be phosphoserine, so that polyphosphoserine molecules are included. However, preferably, if X is phosphoserine, Y is other than phosphoserine. In another preferred embodiment, X is aspartate or glutamate, particularly preferably aspartate. Y is particularly preferably phosphoserine.

By anionic derivatives of the amino acids of X, it is meant that the amino acid (i.e. aspartate, glutamate asparagine, or glutamine) is phosphorylated, sulfated, phosphonated or sulfonated. Preferably, the side chain of the amino acid is treated with an appropriate reagent to result in one or more (e.g. 1–3), preferably one phosphate, sulfate, phosphonate, or sulfonate moiety. If the α-amino group of the peptide is for reaction, it may also be phosphorylated, sulfated, phosphonated or sulfonated. These derivatives can be prepared by the transamidation reaction of *Fong and Kowalski*, U.S. Pat. No. 4,678,840 (1987).

The Y residue may be a phosphorylated amino acid selected from the following group:

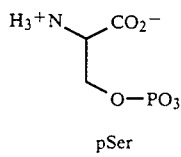

pSer

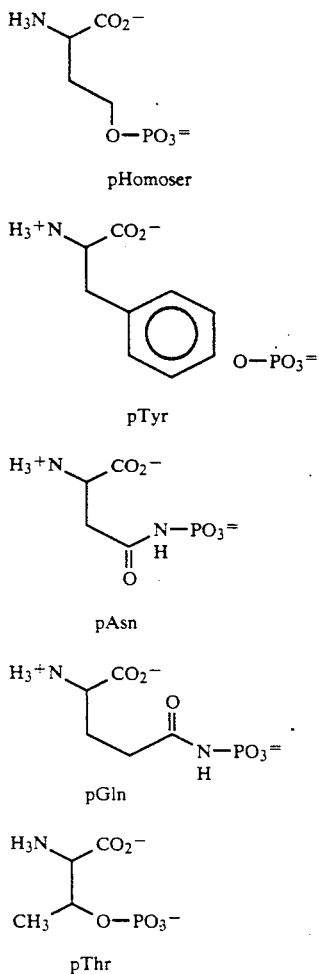

pHomoser pTyr pAsn pGln pThr

The number of Y amino acids, n, is preferably 1-2, particularly preferably 1.

The number of X residues, m, is preferably 10-50, particularly preferably 15-45, most preferably 30-40.

The sum of m+n is preferably greater than or equal to 5, particularly preferably greater than or equal to 10. The maximum of m+n is 153.

The chemical connections between the X residues, the Y residues and the X-Y residues is generally an amide bond, preferably connected by way of the alpha amino and carboxyl groups of two amino acids. However, it is also within the scope of the present invention to have some bonds between the alpha amino group of one amino acid and the beta carboxyl group of an aspartate residue, or between the alpha amino group of one amino acid and the gamma carboxyl group of a glutamic acid residue.

The X and Y amino acid residues are preferably optically active, and will generally be L-amino acids. However, it is also possible for the X and/or Y residues to be D-amino acids, or the peptide/polypeptide molecule may be made up of a combination of D and L residues, such as a racemic mixture. It is preferred that all of the amino acids be L-amino acids or D-amino acids, particularly preferably all L-amino acids.

The X residues may be connected to the Y residues by way of a carboxyl group of an X residue and an amino group of a Y residue (C-terminus X residue), or between a carboxyl group of a Y residue and an amino group of an X residue (N-terminus X residue). Preferably, the X groups will be C-terminus X residues.

The acidic side chains of the amino acid residues making up the present molecules may be in protonated form or may be in a salt form, or a mixture thereof. For example, the aspartate residues may be protonated so that they are aspartic acid residues, and the glutamate residues may be protonated so that they are glutamic acid residues. Similarly, the anionic derivatives of the amino acids may be in anionic form (e.g. sulfate, phosphonate, sulfonate), or may be protonated.

Salts of any of the acidic residues set forth above, especially the sodium and potassium salts, are also within the scope of this invention. When phosphorylated amino acids are incorporated in the compounds, they may be present as salts, e.g., $Ca^{+2} Mg^{+2}$, di-$Na^+$, di-$K^+$, and the like. Such salts may also be with transition metals such as zinc, aluminum, nickel and copper, preferably zinc and aluminum. Further, salts of the amino group, such as the p-toluenesulfonate, acetate, etc. are also contemplated.

With respect to the salt forms of the above-identified molecules, it is to be noted that the zinc and aluminum salts may be preferred, since it is known that zinc and aluminum salts of other molecules can inhibit mineral deposition. For example, U.S. Pat. No. 4,522,806 (1985) by H. R. Muhlemann and I. P. Sayer mentions oral compositions and zinc salts. In addition, U.S. Pat. Nos. 4,100,269 (1978) and 4,152,418 (1979) deal with zinc and toothpaste.

The cations that seem to be the best mineralization inhibitors are $Zn^{2+}$ and $Al^{3+}$; however others such as $Mg^{2+}$, $Cu^{2+}$, and $Ni^{2+}$ have been studied and also appear to be useful. Accordingly, it is contemplated that the present invention is not limited to specific salts mentioned herein, and that other cationic metal salts of the present peptides, particularly cationic transition metal salts, could be formed and used for the purposes described herein.

It is also possible, and within the scope of the present invention, to have physical combinations of compounds of the prior art which are known to inhibit mineralization and one or more of the present compounds. Such compositions may exert a synergistic effect in terms of mineral deposition inhibition. One possible prior art compound which could be included in a composition is zinc citrate.

Particularly preferred subgenuses of compounds and species, which fall within the scope of the above described compounds, are shown hereinbelow.

H-(pSer)$_1$-(Asp)$_{15-45}$-OH, preferably
H—(pSer)$_1$—(Asp)$_{40}$—OH
H—(pSer)$_2$—(Asp)$_{15-45}$—OH, preferably
H—(pSer)$_2$—(Asp)$_{40}$—OH
H—(pSer)$_1$—(pTyr)$_{15-45}$—OH, preferably
H—(pSer)$_1$—(pTyr)$_{40}$—OH
H—(Asp)$_{15-40}$—(pSer)$_1$—OH, preferably
H—(Asp)$_{40}$—(pSer)$_1$—OH
H—(Asp,Glu)$_{15-45}$—(pSer)$_1$—OH (aspartate, glutamate copolymer)
H—(pSer)$_1$—(Asp,Glu)$_{15-45}$—OH etc. (e.g. salts, mixed salts).

The abbreviations used herein are defined as follows:
pSer : phosphoserine
Asp : aspartate, aspartic acid
Glu : glutamate, glutamic acid
Tyr : tyrosine
pTyr : phosphotyrosine pHomoser : phosphohomoserine
pThr : phosphothreonine
pGln : phosphoglutamine
pAsn : phosphoasparagine Methods of synthesis The products of the invention may be synthesized by any number of techniques now available for synthesis of simple and complex low molecular weight polypeptides. Generally speaking, these techniques involve stepwise synthesis by successive additions of amino acids to produce progressively larger molecules. The amino acids are linked together by condensation between the carboxyl group of one amino acid and the amino group of another amino acid to form a peptide bond. To control these reactions, it is necessary to block the amino group of one amino acid and the carboxyl group of the other. The blocking groups should be selected for easy removal without adversely affecting the polypeptides, either by racemization or by hydrolysis of formed peptide bonds. Certain amino acids have additional functional groups such as the carboxyl groups of aspartic acid and glutamic acid and the hydroxyl groups of serine, homoserine and tyrosine. It is usually necessary to block these additional groups with an easily removed blocking agent, so that they do not interfere with the desired condensation for the formation of peptide bonds.

A wide variety of procedures exist for the synthesis of polypeptides, and a wide variety of blocking agents have also been devised. Most of these procedures are applicable to the peptides of the present invention. The preferred method for synthesis of the subject peptides is a solid-phase technique. In this procedure, an amino acid is bound to a resin particle, and the peptide is generated in a stepwise manner by successive additions of protected amino acids to the growing chain. The general procedure is well known, and has been described in many articles, for example: Merrifield, R.B., J. Am. Chem. Soc. 96, 2986–2993, 1964.

A preferred solid-phase method is described hereinbelow.

Solid-phase Peptide Synthesis

An automated, solid-phase peptide synthesizer (Applied Biosystems, Model 430 A) was used to prepare peptides. The t-Boc strategy terminal amine protection was used with aspartic acid supplied as t-Boc-L-aspartic acid with beta carboxyl protection by O-benzyl linkage. Similarly, serine was supplied as t-Boc-L-serine-O-benzyl.

In all cases, coupling efficiency of each residue was checked by automated sampling of peptide resin for measurement of unreacted free amine by the ninhydrin method (Sarin et al. 1981). Coupling efficiencies routinely were greater than 99% per cycle of synthesis.

Following synthesis, peptide-resin was repeatedly washed with methanol then dried and weighed. Then peptides were cleaved from the resin using a modification of the trifluoromethyl sulfonic acid (TFMSA) procedure, with precautions taken to prevent aspartimide formation (Bergot et al. 1986). For 100 mg samples, peptide-resins in a scintillation vial were treated for 10 minutes with 150 μl of anisole to swell the resin, making it more accessible for reaction. Then 1.0 ml of neat trifluoroacetic acid (TFA) was added with magnetic stirring and allowed to react for 10 minutes. Next, 100 μl of concentrated TFMSA (Aldrich Chemical Co.) were added with cooling using an ice bath, followed by cleavage of the peptide from the resin at room temperature for 30 minutes. For cleavage of other amounts of peptide-resin, the amounts of reagents used were changed proportionally.

Following cleavage, 20 ml of methyl butyl ether (MBE) (Aldrich) were added to the vial to ensure precipitation of the peptide, which already was relatively insoluble in the acidic reaction medium due to the acidic nature of the peptides. After stirring for 1–2 minutes, the entire slurry was passed through a 4.25 cm glass fiber filter (Fisher G4) using a filter funnel and vacuum pump at 15 psi. This removed the TFA, TFMSA, anisole, and any soluble reaction products, leaving the cleaved peptide and resin on the filter.

Extraction of Metal Salts of the Peptides

After washing on the filter with 100 ml of MBE, the acid form of the peptides was converted into a soluble sodium salt by extraction into a clean, dry flask with 10 ml of $Na_2CO_3$ (0.02 M, pH 10.2), using 5 successive rinses of 2 ml, with a least 1 minute extraction on the filter prior to applying the vacuum each time. Conversion of the peptides to other metal adducts such as Zn or Al forms may be accomplished by adding an excess of soluble salts of the metals; for example, $ZnCl_2$ or $AlCl_3$, to the $Na_2CO_3$ solution used for the extraction.

Purification of the Peptides

Upon extraction, the filtrate containing the solubilized peptides had pH values >5. The filtrate was then dialyzed twice with stirring against 2 liters of distilled water for 2 hours using dialysis tubing (Spectrapor, nominal MW cutoff of 1000 daltons). The dialysate was frozen and lyophilized, yielding white flakes or powers. The average yield of the peptides was 40%.

Following isolation, purity of the peptides was checked by high performance liquid chromatography (Varian 5500 LC) using gel permeation columns designed for separations of peptides (Toya Soda 2000 SW and 3000 PWXL). Single, sharp peaks at the appropriate MW's were obtained.

Because the peptides were isolated partially as sodium salts, the sodium content was determined by atomic absorption (Perkin ELmer model 360). Sodium levels typically were less than 5% by weight. Amounts of peptides reported were corrected for sodium content. Concentrations of peptides in aqueous stock solution were based on lyophilized dry weight but were also checked by comparison of UV spectra.

References

Bergot, J.B., R. Noble, and T. Geiser. 1986. TFMSA/TFA cleavage and deprotection in SPPS. Applied Biosystems Bulletin.

Sarin, V.K., S.B.H. Kent, J.P. Tam, and R.B. Merrifield. 1981. Quantitative monitoring of solid-phase peptide synthesis by the ninhydrin reaction. Anal.Bioch. 117:147–157.

Thermal Peptide Synthesis

Alternatively, peptides of approximately known sequence and size may be made by thermal polymerization of amino acids (Fox, S.W. and K. Harada, Thermal polycondensation of alpha-amino acids; In, A Laboratory Manual of Analytical Methods of Protein Chemistry, Vol.4, P. Alexander and H.P. Lundgren (eds.), 1966, pp. 127–151). For example, L-aspartic acid (500 g) was placed in a two-liter, round-bottom reaction vessel, originally designed as the evaporator vessel in a rotary evaporator apparatus. The reaction vessel was partially submerged in cooking oil in a deep-fryer set at 190° C./ (±2° C.). The reaction vessel was coupled by ground glass fitting to a condenser vessel, which in turn was fitted to a rotator shaft driven by a rheostated electric motor. The fittings were sealed with tape and fastened with hose clamps. A stream of nitrogen was continuously purged into the condenser vessel to eliminate $O_2$ and the possibility of charring. The reaction was allowed to continue for up to 24 hours at which time no further visible evolution of water vapor was observed. The water is produced as a result of the dehydration reaction of peptide bond formation and serves as a good indicator of the progress of the reaction.

Polyaspartate molecules of approximately 5000 daltons (determined by gel permeation) were produced. They were purified by dissolving at pH 6 in water followed by dialysis to remove unreacted aspartic acid, although the bulk product is also usable without further purification.

Phosphorylation of Peptides

Serine residues attached at either the N-terminus or the C terminus were phosphorylated via the method of Neuhaus and Korkes (1958). Phosphorus oxychloride, $POCl_3$, was added as 117 ml (1.25 moles) to 45 ml (2.5 moles) of water. This solution was stirred for one hour, allowing formation of monochlorophosphate ($ClH_2PO_3$). Next, amounts up to 0.25 moles of peptides were added with stirring and occasional heating at 60° C. for two hours. The reaction was ended by dropwise addition of 18 ml (1 mole) of $H_2O$ to degrade any unreacted monochlorophosphate to orthophosphate. Any polyphosphates that may have formed during the reaction were destroyed by addition of 75 ml of 1N HCl and heating in a boiling water bath for at least 20 minutes. Upon cooling, peptides were crystallized in 95 percent ethanol and methyl butyl ether at 3° C. overnight. Crystals were washed repeatedly with ethanol. The extent of phosphorylation of peptides was monitored spectrophotometrically upon formation of the phosphomolybdate complex (Eisenreich et al., Environmental Letters 9, 43–53 (1975)).

Other useful derivatives are envisioned as well; for example, peptides containing sulfated, phosphonated, and sulfonated residues. In addition, thermal polymers of aspartic acid can be combined with reactive residues like asparagine or serine to produce available sites for derivatizations.

Activity Assays

To measure the ability of the peptides of the present invention to inhibit mineralization, a number of assays have been developed. These assays include the following:

1. pH—drift assay—$CaCO_3$.
2. pH—drift assay calcium phosphate.

The following examples describe how these assays have been employed to measure the ability of the polypeptides to inhibit mineralization.

EXAMPLE 1

The pH-drift assay - Calcium Carbonate

A so supersaturated with respect to $CaCO_3$ is prepared by separately pipetting 0.3 ml of 1.0 M $CaCl_2$ dihydrate and 0.6 ml of 0.4 M $NaHCO_3$ into 29.1 ml of artificial seawater (0.5 NaCl, 0.011 M KCl). The reaction vessel is a 50 ml, 3-necked, round-bottom flask partially immersed in a thermostated water bath at 20° C. The reaction vessel is closed to the atmosphere to minimize exchange of $CO_2$. The reaction is started by adjusting the pH upward to 8.3 by titration of $\mu l$ amounts of 1 N NaOH by digital pipette. The initial concentrations are 8 mM each of $Ca^{2+}$ and dissolved inorganic carbon (DIC). The reaction is monitored by pH electrode and recorded by strip chart.

After a period of stable pH during which crystal nuclei form, the pH begins to drift downward until the reaction ceases due to depletion of reactants and the lowering of pH. The reaction may be quantified by calculations based on DIC equilibria to give the amount of precipitation versus time. In FIG. 1 it can be seen that a change in pH is directly proportional to a change in DIC from pH 8.3 to 7.7, but below 7.7 the buffering effect of the DIC system leads to greater changes in DIC per unit pH.

EXAMPLE 2

The pH-drift assay: Calcium Phosphate

A solution supersaturated with respect to calcium phosphate is prepared by separately pipetting 0.1 ml of 1.32 M $CaCl_2$ dihydrate and 0.1 ml of 0.90 M $NaH_2PO_4$ into 29.8 ml of distilled water. This yields initial concentrations of 4.4 mM $Ca^{2+}$ and 3.0 mM dissolved inorganic phosphorus (DIP). The reaction vessel is a 50 ml, round-bottom, 3-necked flask partially immersed in a thermostated water bath at 20° C. The reaction vessel is closed to the atmosphere. The reaction begins upon mixing the reactants with an initial pH of 7.4.

Figure 2:
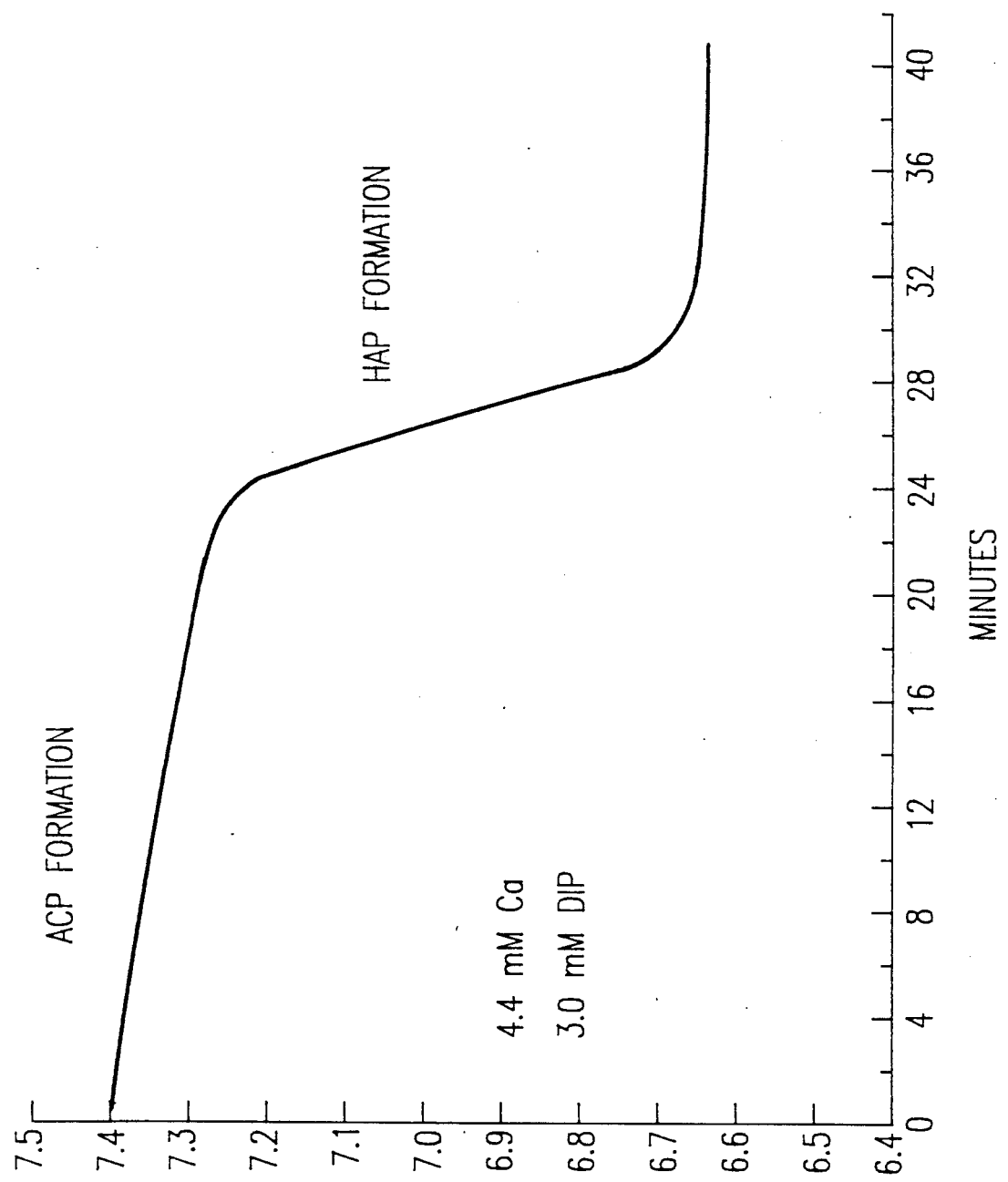
FIG. 2: Data obtained from a calcium phosphate crystallization assay.
Figure 3:
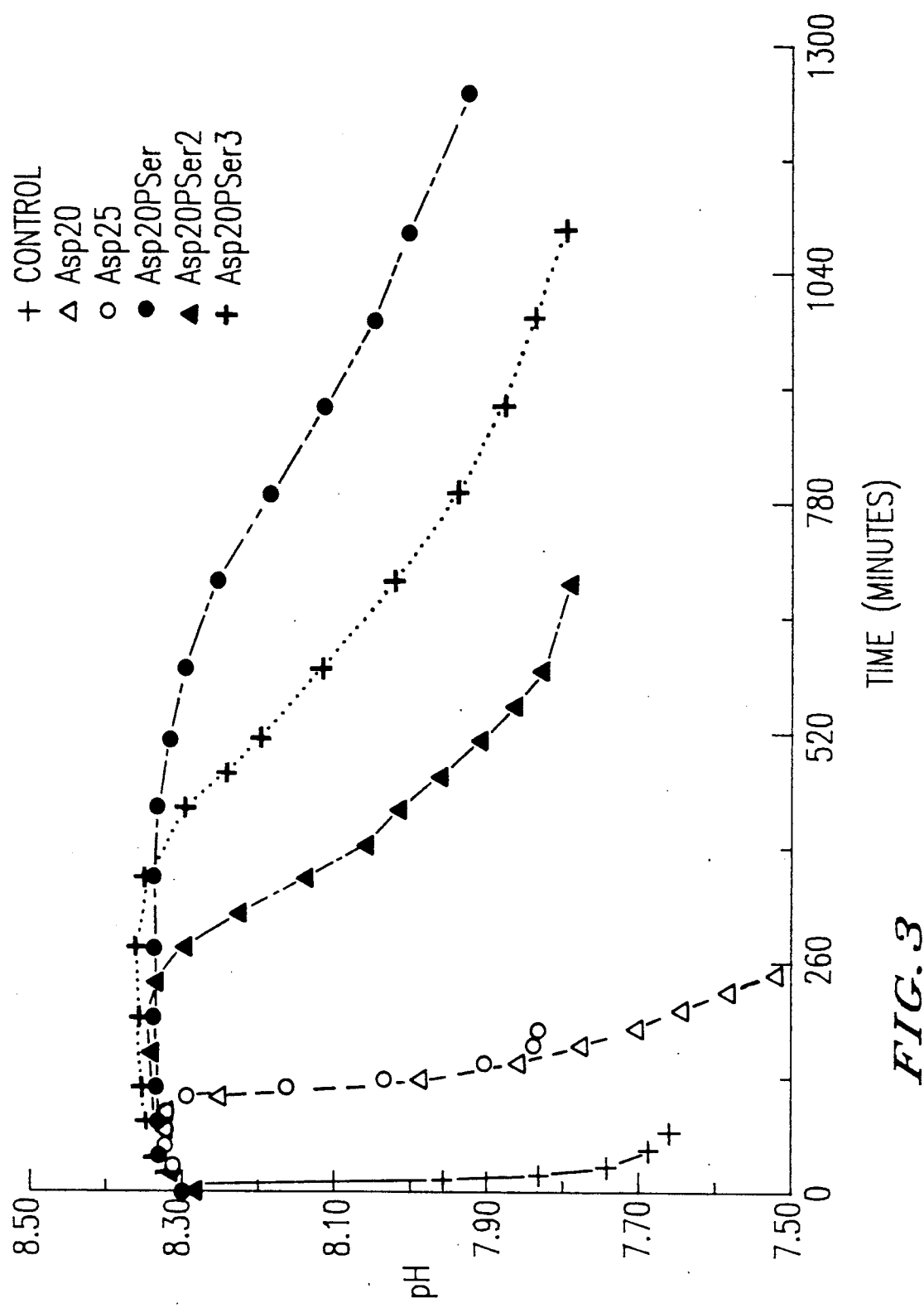
FIG. 3: effects of phosphorylation of synthetic, polyanionic peptides on $CaCO_3$ crystallization.
Figure 4:
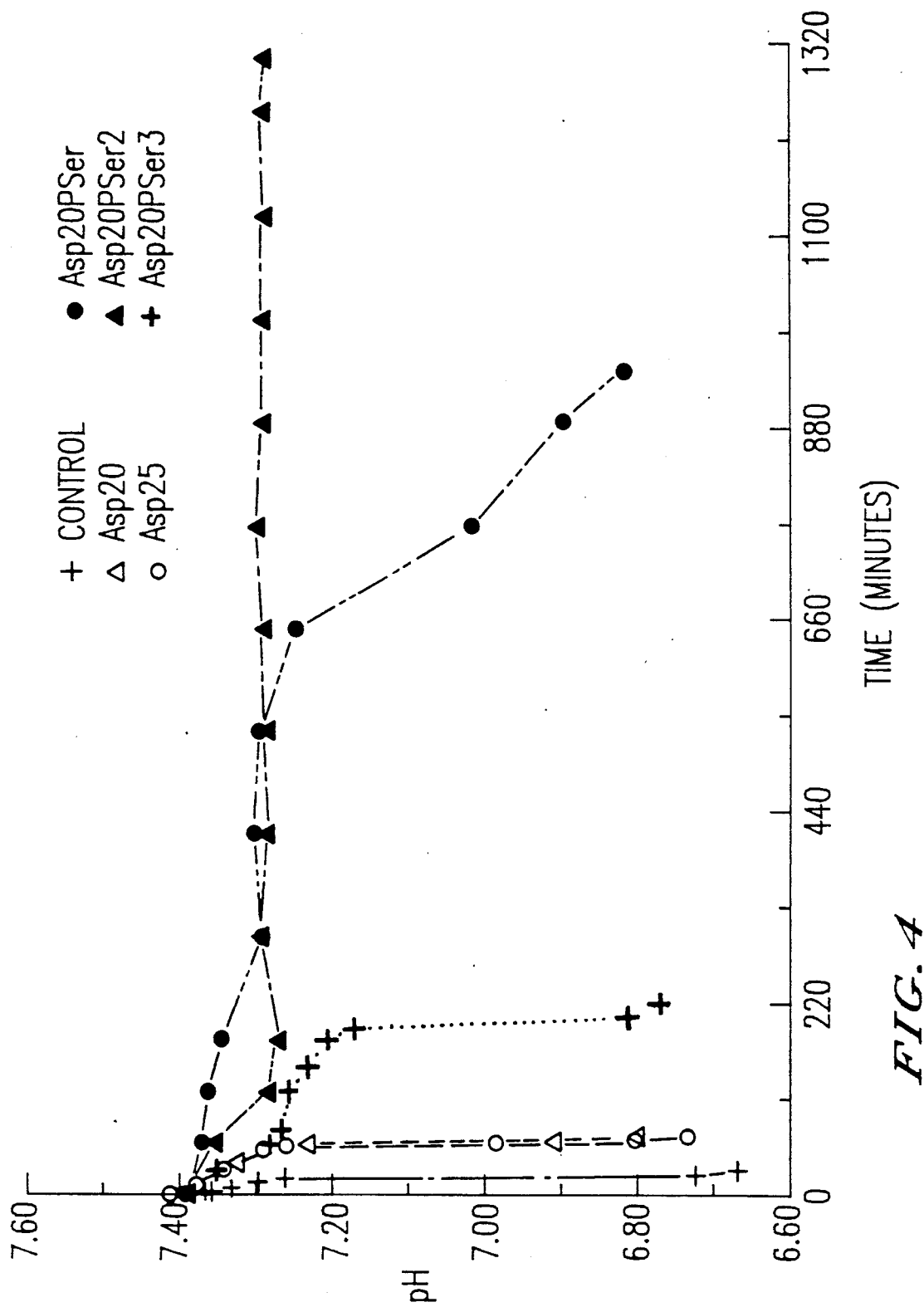
FIG. 4: effects of phosphorylation of synthetic polyanionic peptides on calcium phosphate crystallization.

FIG. 2 shows data obtained from this type of assay. Amorphous calcium phosphate (ACP) nucleates immediately and slowly grows as indicated by a slight decrease in pH during the first 30 minutes or so of the assay. Following this, ACP begins to transform to calcium hydroxylapatite (HAP), $Ca_{10}(PO_4)_6(OH)_2$, as indicated by a marked acceleration in the downward pH drift. The reaction ceases as reactants are depleted and the pH is lowered.

EXAMPLE 3

(FIG. 3)

Effects of phosphorylation of synthetic, polyanionic peptides on $CaCO_3$ crystallization. In all experiments peptides were added in solution at 0.05 $\mu g/ml$. Notice that the polyaspartate molecules that had one to three phosphoserine residues on the end were far more effective inhibitors of $CaCO_3$ formation as indicated by the length of time prior to crystallization, shown by stabilization of pH of the metastable solution at about pH 8.3. Note also that the most effective molecule measured was HO—(Asp)$_{20}$—(pSer)$_1$—H followed by HO—(Asp)$_{20}$—(pSer)$_3$—H and HO—(Asp)$_{20}$—(pSer)$_2$—H. Thus, surprisingly, a single phosphoserine residue at the end of the molecule was the best arrangement, and adding more phosphoserines diminished the activity of the molecules.

EXAMPLE 4

(FIG. 4)

Effects of phosphorylation of synthetic, polyanionic peptides on calcium phosphate crystallization.

In these experiments, the concentration of peptides in solution was 30 $\mu g/ml$. The inhibitory activity of the peptides was shown by the degree to which they stabilized the downward pH-drift as calcium phosphate crystals grow. The polyaspartate molecules having one to three phosphoserine residues on the end were by far the most effective molecules. In calcium phosphate inhibition, HO—(Asp)$_{20}$—(pSer)$_2$—H was clearly the most effective molecule, followed by HO—(Asp)-

$_{20}$—(pSer)$_1$—H, with HO—(Asp)$_{20}$—(pSer)$_3$—H having much less activity, although still considerably more than simple HO—(Asp)$_{20}$—H or HO—(Asp)$_{25}$—H molecules. However, as shown in Example 3, the serine residues of the HO—(Asp)$_{20}$—(pSer)$_3$—H molecules were incompletely phosphorylated due to limitations of the method of phosphorylation. In any event, it is clear that having one or two phosphoserine residues at the end of a polyanionic peptide greatly enhances inhibitory activity.

EXAMPLE 5

Comparison of phosphorylated and non-phosphorylated serine-containing peptides as inhibitors of calcium carbonate and calcium phosphate formation.

That data (Table 1) indicate that, in all cases, the presence of phosphoserine residues enhances the inhibition of crystallization by the peptides. However, it seems that the greatest enhancement was observed when only one or two phosphoserine residues were placed at the end of a polyaspartate molecule. The attempt to place three phosphoserine residues at the end was not completely successful in that it was difficult and perhaps not possible to phosphorylate all three residues, apparently for steric reasons. Similarly, it was possible only to phosphorylate 20 to 30 percent of residues in polyserine or serine-enriched peptides other than the HO—(Asp)$_{20}$—(Ser)$_{1-3}$—H peptides, again probably due to limitation of access of the phosphorylating agent to the phosphorylation sites.

amino acid polymers of this invention can be added to water, water-containing liquids or other liquids in an amount as small as 0.01 ng/ml. The upper limit for the amount of the inhibitor is generally only given by its solubility in the liquid to which it is added. However, if the presence of insoluble residues of these polymers does not interfere with industrial operations, it may be desirable to add these inhibitors in an amount greater than that given by their solubility limit.

A preferred range of the various peptide derivatives for controlling inorganic scaling of e.g., calcium carbonate is $10^{-4} - 10^2$ $\mu$g/ml. Other preferred ranges are $10^{-4} - 0.1$ $\mu$g/ml and $0.1 - 10^2$ $\mu$g/ml of the 1 various-polymeric derivatives.

When the present inhibitors are utilized for their antifouling characteristics in order to prevent the encrustrations of plant or animal organisms, they can be added to a liquid such as water, water-containing liquids or other non-aqueous liquids, preferably in an about 0.001–1,000 $\mu$g/ml, although larger amounts can also be used. Used within this range of concentrations, the present inhibitors find an application in the prevention of encrustration of organisms in, e.g., running water piping or sewage piping, among others.

The present inhibitors can also be applied directly to a surface before it comes in contact with mineral containing liquids, e.g., industrial containers, marine surfaces such as those in piers, ships, and the like. The present inhibitors may be applied by themselves or in combination with other salt deposition inhibitors, an-

TABLE 1

Effects of Phosphorylation on CaCO$_3$ and CaPO$_4$ Crystallization

| Peptide[d] | % Ser as PSer | Calcium Carbonate Assay[a] | | Calcium Phosphate Assay[b] | |
|---|---|---|---|---|---|
| | | (ug/ml) | Induction Period (minutes) | (ug/ml) | Period to Apatite formation (minutes) |
| Control | | | 5.86 ± 0.76[c] | | 20.7 ± 2.09[c] |
| PolySer(mw 5100) | | 0.05 | 4.00 ± 0.28 | 10 | same as control |
| PolyPSer | 23.0 | 0.05 | 113 ± 50.6 | 10 | 33.5 ± 8.74 |
| (AspSerGly)$_{10}$ | | 0.10 | 9.10 ± 1.20 | 10 | same as control |
| (AspPSerGly)$_{10}$ | 30.0 | 0.10 | 7.50 ± 2.10 | 10 | 28.0 ± 1.70 |
| (AspSer)$_{10}$ | | 0.05 | 33.5 ± 2.12 | 10 | same as control |
| (AspPSer)$_{10}$ | 29.0 | 0.05 | 205 ± 14.4 | 10 | 31.0 ± 2.80 |
| Asp$_{20}$ | | 0.05 | 87.5 ± 19.0 | 30 | 59.7 ± 6.40 |
| Asp$_{20}$Ser | | 0.05 | 65.0 ± 11.1 | 30 | 47.3 ± 3.05 |
| Asp$_{20}$PSer | 97.6 | 0.05 | 583 ± 5.80 | 30 | 601 ± 103 |
| Asp$_{20}$Ser$_2$ | | 0.05 | 48.8 ± 16.2 | 30 | 54.5 ± 3.50 |
| Asp$_{20}$PSer$_2$ | 99.8 | 0.05 | 254 ± 39.9 | 30 | >20 hours |
| Asp$_{20}$Ser$_3$ | | 0.05 | 31.3 ± 11.1 | 30 | 53.0 ± 0.75 |
| Asp$_{20}$PSer$_3$ | 59.0 | 0.05 | 326 ± 88.0 | 30 | 185 ± 9.30 |

[a]CaCO$_3$ pH-drift assay: 10 mM Ca$^{2+}$, 8 mM dissolved inorganic carbon, 30 ml artificial seawater, 20° C., initial pH = 8.30.
[b]CaPO$_4$ pH-drift assay: 4.4 mM Ca$^{2+}$, 3 mM dissolved inorganic phosphorus, 30 ml distilled water, 20° C., initial pH = 7.40.
[c]Mean values ± standard deviations, n = 3 to 70.
[d]The amino terminus of these peptides is on the right-hand side (e.g. Asp$_{20}$Ser = HO—Asp—(Asp)$_{19}$—Ser—H).

Uses of the Present Polypeptides

The various polypeptides of this invention may be utilized directly without additives or carriers for inhibiting the deposition of minerals such as phosphates and carbonates whether of inorganic or biological origin. Uses for inhibition of other salts of carbonate, phosphate and sulfate, e.g., magnesium or barium slats, are contemplated. The various polypeptides may be utilized by adding an effective amount of the inhibitor to a liquid in contact with a surface on which the deposits may form. Such is the case of industrially useful and commercially important containers, i.e., boilers, piping, desalinators, cooling towers, and the like. The various tirust agents, or the like and/or with a carrier, directly to the exposed surface, or they may be mixed with other polymers used for the protection of said surfaces. A variety of carriers are contemplated for the application of the present inhibitors. Some of the most common carriers include aqueous and non-aqueous liquids, gels, oils, organic and inorganic solvents, compressed gases, and the like. However, any carrier may be used according to the needs. When used in high concentrations by themselves, the poly amino acid inhibitors of this invention may be highly viscous and can be easily applied to a surface.

After the application of the inhibitors, an appropriate length of time may be allowed for the penetration of the inhibitor into the surface, as is the case with porous surface materials, such as wood, ceramics and the like. Thus, a large storage of the present inhibitors is created within the material and the surface may then be partially sealed with a coat-forming polymer to retard release of the active component.

Alternatively, the various polypeptides may be mixed with a carrier to form a suspension which can be applied to a surface. The present inhibitors may be applied to any type of surface which may be exposed to the formation of inorganic or biological mineral deposits. Some of the most common materials to which the present inhibitors may be applied are metals, woods, synthetic polymers and copolymers, glass, ceramics, and painted or otherwise coated surfaces, although other materials are also contemplated. When in contact with the mineral-containing liquid, the inhibitors will slowly leach out from underneath the polymeric coating layer. The present inhibitors may further be applied in admixture with the coating forming polymer, e.g., paints or any synthetic polymer used for the protection of surfaces such as polyurethanes. When the present inhibitors are used in admixture with a coat-forming polymer, they can be sued in a concentration of between 0.001-90% by weight of the total composition, although higher or lower concentrations are also contemplated in this invention. Some of the preferred concentrations are 1-75% by weight. Other preferred concentrations are 5-25%, 25-50% and 10-40% by weight. When applied to a surface the present inhibitors may be formulated with a carrier in the form of powder, solution, suspension, gel, oil, aerosol, paste or viscous colloid.

In a preferred embodiment of the present invention, the present materials may serve as inhibitors of dental tartar and plaque formation (referred to herein as tartar barrier agents) for human or animal use. In accordance with this embodiment of the present invention, the oral compositions may comprise any conventional pharmaceutically acceptable oral hygiene formulation that contains and is compatible with an effective amount of an antidental calculus agent as disclosed herein. Such formulations include, for example, mouthwashes, rinses, irrigating solutions, abrasive and non-abrasive gel dentifrices, denture cleansers, coated dental floss and interdental stimulator coatings, chewing gums, lozenges, breath fresheners, foams and sprays. These formulations may be used to treat natural or artificial tooth enamel, or any orally compatible material which is subject to mineral deposition. Although human use is preferred, use in animals is also possible.

The tartar barrier agents may be present in the formulations in effective concentrations generally in the range of from about 0.05 wt.% to as much as 30 wt.% or the limit of compatibility with a vehicle. A preferred concentration range for the agents of the formulations of the invention is from about 0.5 to about 10 wt.%. A more preferred range is from about 2 to about 8 wt.%.

The metal salts of the peptides of the present invention can be included in compositions up to the limit of their solubility therein, preferably around 0.2 to 2%, with 10% being a reasonable maximum limit, by weight. In addition, the peptides of the present invention may be used in their acid forms, or as, for example, sodium salts, alone or in combination along with inorganic salts which are known by the prior art to be inhibitors of mineralization. The combined percentage of these materials, which together operate as anticalculus agents, can be included in the composition in concentrations of from 0.2 to 10%, by weight, preferably around 2% by weight.

The pH of these preparations should be between about pH 5 and 10, preferably between pH 5 and 8, more preferably between about 6 and 7.5. A pH lower than 5 is undesirable because of the possible enhancement of enamel demineralization.

Suitable conventional pharmaceutically acceptable vehicles that can be employed with the tartar barrier agents to prepare the compositions of this invention may comprise water, ethanol; such humectants as polypropylene glycol, glycerol and sorbitol; such gelling agents as cellulose derivatives, for example, Methocel carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example Cab-O-Sil M5, and polyvinylpyrrolidone; sweeteners such as sodium saccharin and aspartame; preservatives such as citric acid, sodium benzoate, cetylpyridinium chloride, potassium sorbate, methyl and ethyl parabens; detergents such as sodium lauryl sulfate, sodium cocomonogylceride sulfonate, sodium lauryl sarcosinat and polyoxyethylene isohexadecyl ether (Arlasolve 200) and approved colors and flavors.

The following specific examples will serve further to illustrate the tartar barrier agent compositions of this invention.

EXAMPLE A - Mouthwash Solution

| | |
|---|---|
| Tartar barrier agent | 0.5-2.0% w/w |
| Glycerol (Humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B - Mouthwash Solution

| | |
|---|---|
| Tartar barrier agent | 0.5-3.0% w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C - Abrasive Dentifrice Gel

| | |
|---|---|
| Tartar barrier agent | 2.0-10.0% w/w |
| Fumed Silica (abrasive) | 55.0 |
| Sodium Lauryl Sulfate (detergent) | 1.5 |
| Glycerol (Humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.00 |

EXAMPLE D - Chewing Gum

| | |
|---|---|
| Tartar barrier agent | 1.0-11.0% w/w |
| Gum Base | 21.3 |
| Sugar | 48.5-58.5 |

| -continued | |
|---|---|
| Corn Syrup (Baume 45) | 18.2 |
| Flavors | 1.0 |
| | 100.00 |
| EXAMPLE E - Nonabrasive Gel Dentrifice | |
| Tartar barrier agent | 0.05–30.0% w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium saccharin | 0.2 |
| Flavors | 1.5 |
| | 100.0 |

In addition to the above materials which can be included in the present tartar barrier compositions, it is also contemplated to include therein a protease inhibitor to prevent the present peptides and polypeptides from being degraded by various proteolytic enzymes.

Examples of such inhibitors include aprotinin and trypsin inhibitor types I-P, I-S, II-L, II-O, II-S, IIT, III-O, and IV-O, although other inhibitors are within the scope of this invention. Similarly, when phosphopeptides are employed, it is contemplated to use phosphatase inhibitors in conjunction with the polypeptide to prevent or inhibit dephosphorylation of the polypeptides. Examples of such phosphatase inhibitors are sodium fluoride, adenosine diphosphate, and vinyl ether/maleic acid polymers (gantrez). Use of other phosphatase inhibitors is also possible.

The present peptides and polypeptides could also be linked to antibodies, particularly those against cavity-causing bacteria, or the antibodies could be added to a tartar barrier composition to enhance antibacterial activity.

The polypeptides of the present invention may also find suitable use in treatment and prevention of mineral buildups in arteries and veins, such as in atherosclerosis.

In this connection, the mode of administration of the polypeptides is preferably parenteral, i.e., intravenous, intraperitoneal, intramuscular, or subcutaneous, with intravenous administration being most preferred. They may be administered alone, without a carrier vehicle; however, they may also be administered with pharmaceutically acceptable nontoxic carriers, the proportions of which are determined by the suitability and chemical nature of the particular carrier. For intravenous or intramuscular administration, they may be used in the form of a sterile solution containing other solutes, for example, sufficient saline or glucose to make the solution isotonic. Like insulin, the peptides of the subject invention may also prove to be administrable by use of a continuous perfusion device, which should simplify the method of administration.

The physician will determine the dosage which will be most suitable for a particular situation. Dosages will generally depend upon the age and size of the patient, and the seriousness of the condition to be treated. A normal dosage will generally be in the range of 200–600 mg peptide per day.

The polypeptides of the present invention can also be used to impregnate prosthetic devices. For example, the polypeptides of the present invention could be incorporated into polymeric based (e.g. a copolymer of ethylene - vinyl acetate or a silicon rubber) controlled released drug delivery matrices for site specific therapy directly into the perianular region of the heart prosthesis (Levy, R.J. et al., CRC Critical Reviews in Biocompatibility 2, 148-187 (1986)). Controlled release devices incorporating a phosphonate derivative have been formulated to deliver that drug for more than 30 years without depletion. In addition, valve cusps could also be preloaded with a polypeptide according to the present invention via covalent aldehyde-amino linkages; such an approach could be useful as a primary anti-calcium measure or as an adjunct for priming controlled release anti-mineralization therapy.

Each of the publications and patents cited herein is hereby incorporated by reference into this application, the same as if the entire disclosure thereof were reproduced directly herein.

The invention now being fully described, it will be apparent to one of ordinary skill in the art that many changes and modifications can be made thereto, without departing from the spirit or scope of the invention as set forth therein.

What is claimed as new and desired to be secured by Letters Patent of the United States is:

1. A poly-amino acid compound, which has the structure:

$$\text{poly } (X)_m(Y)_n$$

where
  each X independently is aspartate, glutamate, glutamine, asparagine, or anionic derivatives of these amino acids, or phosphoserine, or a mixture thereof,
  each Y independently is phosphoserine, phosphohomoserine, phosphotyrosine, phosphoglutamine, phosphoasparagine, phosphothreonine, or a mixture thereof,
  m is 2 to 150,
  n is 1 to 3,
  n+m is >5, and
salts thereof.

2. A compound according to claim 1, in which the first X residue is at the C-terminal of said compound and the last Y residue is at the N-terminal of said compound.

3. A compound according to claim 1, in which the first X residue is at the N-terminal of said compound and the last Y residue is at the C-terminal of said compound.

4. A compound according to claim 1, having a formula selected from the group consisting of:
  H—(pSer)$_1$—(Asp)$_{15-45}$—OH,
  H—(pSer)$_2$—(Asp)$_{15-40}$—OH,
  H—(pSer)$_1$—(Glu)$_{15-45}$—OH,
  H—(Asp)$_{15-40}$—(pSer)$_1$—OH, and
  H—(Asp,Glu)$_{40}$—(pSer)$_1$—OH.

5. A compound according to claim 4, which is:
  H—(pSer)$_1$—(Asp)$_{40}$—OH.

6. A compound according to claim 4, which is:
  H—(pSer)$_2$—(Asp)$_{40}$—OH.

7. A compound according to claim 4, which is:
  H—(pSer)$_1$—(Glu)$_{40}$—OH.

8. A compound according to claim 1, wherein m=20—40 and n=2–3.

9. A compound according to claim 1, wherein said aspartic acid and glutamic acid residues are in the form of sodium, potassium, zinc or aluminum salts, or mixtures thereof.

10. A compound according to claim 1, wherein said phosphoserine, phosphohomoserine, phosphotyrosine, phosphoglutamine, phosphoasparagine, and phosphothreonine residues are in the form of disodium, dipotassium, calcium or magnesium salts.

11. A method of inhibiting the deposition of a mineral en a surface, which comprises contacting said surface with a mineral deposition inhibiting effective amount of a compound according to claim 1.

12. A method according to claim 11, wherein said surface is enamel of a tooth.

13. A method according to claim 11, wherein said surface is of a prosthetic device for implantation in vivo.

14. A method according to claim 13, wherein said prosthetic device is a heart valve.

15. A method according to claim 11, wherein said compound is added to a liquid in contact with an industrial container.

16. A method according to claim 11, wherein said compound is coated on or impregnated into a surface which is ordinarily in contact with a marine environment.

17. A composition for inhibiting deposition of mineral on an enamel surface of a tooth, which comprises a mineral deposition inhibitory effective amount of a compound according to claim 1, in combination with an orally acceptable vehicle compatible with said compound.

18. A composition according to claim 17, in the form of an oral hygiene formulation selected from the group consisting of mouthwashes, mouthrinses, irrigating solutions, abrasive gel dentifrices, nonabrasive gel dentifrices, denture cleansers, coated dental floss, coated interdental stimulators, chewing gums, lozenges, breath fresheners, foams and sprays.

19. An aqueous solution, comprising a crystallizable inorganic mineral, and a mineral crystallization inhibitory amount of a compound according to claim 1, wherein said inorganic mineral would crystallize in the absence of said compound.

* * * * *